US007610157B2

(12) United States Patent  (10) Patent No.: US 7,610,157 B2
Miller et al.  (45) Date of Patent: Oct. 27, 2009

(54) APPARATUS AND METHOD FOR FULLY AUTOMATED CLOSED SYSTEM PH MEASUREMENT

(75) Inventors: Peter Miller, New London, CT (US); Andrew Michael Leach, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 215 days.

(21) Appl. No.: 11/858,573

(22) Filed: Sep. 20, 2007

(65) Prior Publication Data

US 2008/0275654 A1  Nov. 6, 2008

Related U.S. Application Data (63) Continuation-in-part of application No. 11/743,288, filed on May 2, 2007, now Pat. No. 7,519,492.

(51) Int. Cl.
 *A61B 5/05* (2006.01)
(52) U.S. Cl. ......................................... 702/31; 600/361
(58) Field of Classification Search ............ 702/31, 702/22–24, 27, 28, 30; 222/1; 600/361, 600/322, 323, 326, 333
 See application file for complete search history.

(56) References Cited

U.S. PATENT DOCUMENTS

| 4,483,927 | A | 11/1984 | Takekawa |
|---|---|---|---|
| 5,073,720 | A | 12/1991 | Brown |
| 6,234,997 | B1 | 5/2001 | Kamen et al. |
| 6,342,948 | B1 | 1/2002 | Gilby |
| 6,466,814 | B1 | 10/2002 | Ardenkjaer-Larsen et al. |
| 6,741,365 | B2 | 5/2004 | Curtis |
| 2002/0001078 | A1 | 1/2002 | Gobel et al. |
| 2006/0127352 | A1* | 6/2006 | Hubbell et al. ........... 424/78.27 |
| 2006/0129036 | A1* | 6/2006 | Lucassen et al. ............ 600/315 |
| 2007/0038041 | A1* | 2/2007 | Yang et al. .................. 600/310 |
| 2007/0260491 | A1 | 11/2007 | Palmer et al. |
| 2009/0084175 | A1* | 4/2009 | Raghuraman et al. .... 73/152.18 |

OTHER PUBLICATIONS

PCT Search Report—Sep. 3, 2008.

* cited by examiner

*Primary Examiner*—Edward Raymond
(74) *Attorney, Agent, or Firm*—Eileen Walsh Gallagher (57) ABSTRACT

The present invention provides an apparatus and method for a noninvasive optical determination of the pH of a substance in a compartment in a closed system comprising a compartment wherein a substance resides which is permeable to at least one wavelength of light, a light source and light detecting device configured to obtain spectral data for a substance for at least one wavelength, a processor adapted to determine the pH of the substance by correlating the spectral data with predetermined spectral data for a known substance at a known pH at the at least one wavelength, and wherein the processor is further configured to control the release of the substance from the compartment to its end use.

25 Claims, 6 Drawing Sheets

APPARATUS AND METHOD FOR FULLY AUTOMATED CLOSED SYSTEM PH MEASUREMENT

REFERENCE TO RELATED APPLICATION

This application is a Continuation in Part (CIP) of U.S. patent application Ser. No. 11/743,288 entitled "APPARATUS AND METHOD FOR FULLY AUTOMATED CLOSED SYSTEM QUALITY CONTROL OF A SUBSTANCE", filed 2 May 2007, which is herein incorporated by reference.

BACKGROUND

This invention is directed to a method and system determining the pH of a substance. More specifically, it relates to noninvasive optical pH measurement of a substance, where physical contact of the substance is undesirable.

Quality Control (hereinafter "QC") devices and methods have become an increasingly important part of industry and healthcare over the last few decades. Typically, QC devices utilize invasive methods such as testing with probes, and/or substance withdrawal techniques to assess whether the substance meets its threshold guidelines. However, invasive techniques like the ones employed in many QC apparati are not suitable for applications that require a substance to be part of an entirely closed system, or where substance loss is undesirable.

Specifically as it relates to healthcare, QC has traditionally occurred at the site of the manufacturer, as opposed to the point of use. However, with the development of new contrast agents and other unstable pharmaceutical products, it may be necessary to perform compounding or processing steps immediately prior to administration into the patient. Prior to injection, the safety and efficacy of the substance must be ensured.

In such a QC apparatus, ensuring the safety and efficacy of the pharmaceutical product being tested may occur by acquiring, for instance, the pH, temperature, concentration and/or volume of the agent while comparing those values to proper end-use values prior to administration, all without the substance leaving a closed system. In addition, a QC system that was entirely closed may operate directly at a patient's bedside, potentially obviating the need of a bedside pharmacist.

One particularly important QC parameter may be the measure of the degree of acidity or alkalinity (pH) of the substance. Methods and devices that have been commonly used to measure the pH of solutions include litmus paper tests, pH electrodes, and pH indicator dye. While these methods may be accurate and robust, they are undesirable in situations that require complete sterility, particularly fast response time, or where substance loss is a concern (i.e., closed system bedside QC devices).

For instance, in the context of a bedside QC device, use of a pH dye may be problematic in that the addition of a non-active ingredient to a pharmaceutical product may have harmful implications to the patient. With regards to pH probes in QC devices, similar issues arise. The sterility of the pharmaceutical must be ensured, and the use of a probe heightens the opportunity for the substance to become contaminated. Furthermore, the above-mentioned techniques are not ideal for applications in which the substance being tested is expensive, where even the smallest amount of substance loss significant.

The use of optics to measure physical properties of a substance is well known. For example, absorption spectroscopy has been used to measure the concentration of ions such as calcium blood and ultraviolet/visible absorption spectroscopy is often used to detect the molecular content in liquid samples. However, the use of optics to rapidly determine the pH of a substance that is entirely part of a closed system would be desirable.

Therefore, what is needed is a noninvasive, optically based method and system to determine the pH of a solution, thereby obviating the need for invasive techniques such as pH probes and indicator dyes that may contaminate a substance or pharmaceutical product.

BRIEF DESCRIPTION

In a first aspect, the invention provides a noninvasive optical method for determining the pH of a substance in a compartment. The method comprises obtaining spectral data for the substance in the compartment for at least one wavelength, correlating the obtained spectral data with spectral data of previously tested solutions of the substance having known pH at the at least one wavelength, determining the pH of the substance in the compartment using a correlation step, and controlling the release of the substance from the compartment to its end-use based on the determined pH value.

In a second aspect, the invention provides a system for determining the pH of a substance. The system comprises a compartment where a substance resides which is permeable to at least one wavelength of light, a light source and light detecting device configured to obtain spectral data for a substance for at least one wavelength, a processor adapted to determine the pH of the substance by correlating the spectral data with predetermined spectral data for a known substance at a known pH at the at least one wavelength, and wherein the processor is further configured to control the release of the substance from the compartment to its end-use.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

The following detailed description is exemplary and not intended to limit the invention of the application and uses of the invention. Furthermore, there is no intention to be limited by any theory presented in the preceding background of the invention or the following detailed description of the drawings.

As used herein, "adapted to," "coupled," and the like refer to mechanical, structural or optical connections between elements to allow the elements to cooperate to provide a described effect.

While this invention is particularly directed to the art of fully automated non-invasive optical pH measurement, it will be appreciated that the invention may have usefulness in other fields. For example, the invention will also find useful application in a wide range of environments where non-invasive and comprehensive measurements of pH values are desired.

In a first embodiment, the invention provides a noninvasive optical method for determining the pH of a substance in a compartment. The method comprises, obtaining spectral data for the substance in the compartment for at least one wavelength, correlating the obtained spectral data with spectral data of previously tested solutions of the substance having known pH at the at least one wavelength, determining the pH of the substance in the compartment using a correlation step, and controlling the release of the substance from the compartment to its end-use based on the determined pH value.

In a second embodiment, the invention provides a system for determining the pH of a substance. The system comprises a compartment where a substance resides which is permeable to at least one wavelength of light, a light source and light detecting device configured to obtain spectral data for a substance for at least one wavelength, a processor adapted to determine the pH of the substance by correlating the spectral data with predetermined spectral data for a known substance at a known pH at the at least one wavelength and wherein the processor is further configured to control the release of the substance from the compartment to its end-use.

Figure 1:
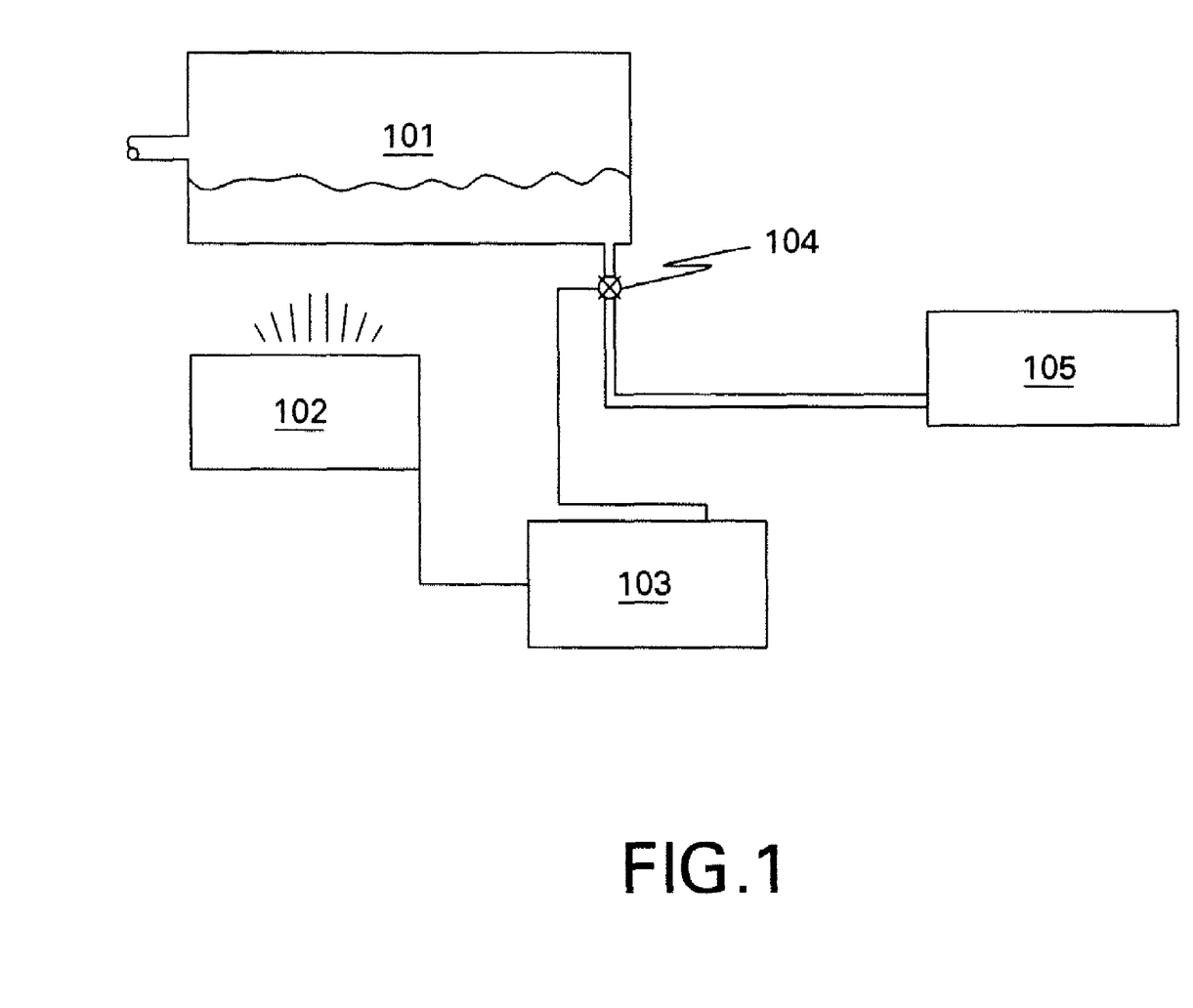
FIG. 1 is a block diagram of a QC device to which embodiments of the present invention are applicable.

Referring to FIG. 1, there is shown a block diagram of a QC apparatus for which embodiments of the present invention are applicable. The QC apparatus comprises a compartment 101, in which a substance may be collected. As used herein, the term "substance" comprises any liquid or gaseous solution. However, the term "substance" may also comprise liquid crystals, colloidal dispersions, plasmas, solid suspensions, amorphous solids, or any combination thereof. For automated QC of a substance in the compartment 101, a monitoring device 102 is coupled to the compartment 101 and is configured to gather optical, thermal, physical and/or chemical information about the substance. The processor 103 is coupled (e.g., optically, electrically, magnetically) to the monitoring device 102, and is configured to receive data from the monitoring device 102. The processor 103 is further configured to perform a comparative analysis on the substance in the compartment 101. A comparative analysis comprises computing applicable QC values, including but not limited to pH, substance identity, concentration, volume, liquid-state polarization, and temperature and comparing at least one QC value against an at least one end-use acceptable value. A release mechanism 104 may function with the compartment 101 to allow for the release of the substance, the release mechanism 104 being further coupled the processor 103. The processor 103 may be further configured to transmit a signal to a release mechanism 104, wherein the release mechanism 104 may release the substance from the compartment 101 to its end-use 105 when a set of one or more end-use acceptable values is obtained. As used herein, "QC value," "QC parameter" and the like refers to any property of a substance that may be the subject of testing e.g. temperature, pH, volume, concentration, liquid-state polarization, density, identity, mass, etc. As used herein, "end-use acceptable value," "end-use value" and the like refers to a specific value e.g. 100° C., 100 mL, any range of values e.g. 100-110° C., 100-110 mL or an upper or lower bound e.g. greater than 100° C., or less than 100 mL.

The compartment 101 may be any of any useful shape or size. In an embodiment of the present invention, the compartment 101 is a rectangular in shape. However, in other embodiments the compartment may be spherical or conical in shape, or contain inflow and outflow tubes where the substance may also be held. If the compartment is an optical block designed to cradle a receiving apparatus (not shown in FIG. 1), the shape and size of the apparatus may match the shape and size of the optical block. Furthermore, in accordance with embodiments of the present invention, the compartment 101 may be assembled with a transparent material, or may contain at least two parallel or opposing windows transparent to one or more wavelengths of light. For example, the monitoring device 102 may transmit light through one window of the compartment 101, and may detect the light transmitted through a parallel window. If, however, the compartment is made entirely of transparent material, the monitoring device 102 may transmit light through one side of the compartment 101 and detect it on a parallel side. If fluorescence is used, detection of light may occur at alternative angles (e.g., 90 or 180) of the compartment. Additionally, in more specific embodiments, the compartment 101 may be composed entirely of a low thermal mass material, such as thin glasses or plastics (e.g. Polymethyl methacrylate, polycarbonate, polystyrene, quartz, etc.) to allow for more accurate noninvasive temperature measurement.

Figure 2:
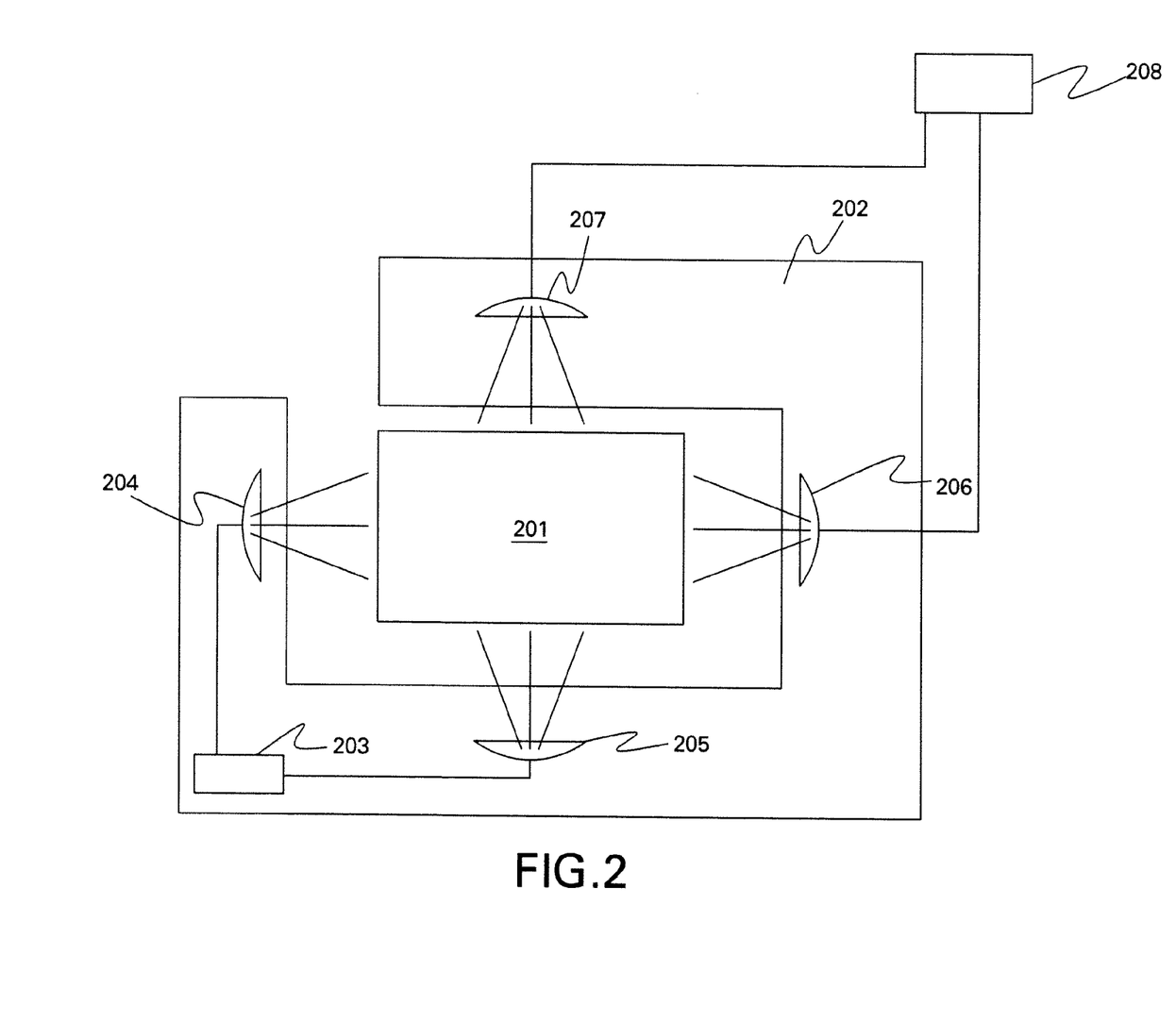
FIG. 2 is a more detailed block diagram depicting an exemplary embodiment of a QC device, and further depicting exemplary elements of the monitoring device.

The monitoring device 102 may comprise a plurality of devices, each functioning in either a separate capacity or in conjunction with one another to measure the intrinsic properties of a substance. With reference to FIG. 2, an embodiment of a monitoring device 202 is shown, which may be configured to gather data about the substance in compartment 201, and may be further configured to transmit the data to the processor 208. The processor 208, using the information received from the monitoring device 202, may be configured to calculate chosen QC values. In embodiments of this particular invention, the pH may be found. However, the processor may also calculate other QC parameters (e.g., pH, volume, temperature, concentration, liquid-state polarization, etc.) and run a comparative analysis.

In the embodiment shown in FIG. 2, monitoring device 202 comprises one or more of a plurality of devices located within the monitoring device. In one exemplary embodiment, monitoring device 202 comprises a first light source 203 that may be fiber optics based, to allow for measurements to be taken from different dimensions of the compartment 201. For instance, light source 203 may be connected fiber optically to light transmitter 204 and 205, wherein each light transmitter may be configured to transmit light through a first and second dimension of the compartment 201. In this particular embodiment, light transmitter 204 may transmit light through the x-axis of the compartment 201 and light transmitter 205 may transmit light through the y-axis of the compartment 201. Alternatively, two separate light sources may also be used to transmit light, each positioned on different dimensions of the compartment 201. The at least one light source 203 may also comprise light emitting diodes (LEDs), lasers, halogen or deuterium lamps, etc.

Referring further to FIG. 2, a first light detector 206 and a second light detector 207 may be positioned to detect the light transmitted from light transmitters 204 and 205 respectively, after the light passes through compartment 201. For example, light detector 207 may be positioned to detect light from light transmitter 205 on the y-axis, and light detector 206 may be positioned to detect light from light transmitter 204 on the x-axis of the compartment 201. Light detectors 206 and 207 are coupled, e.g. electronically, to processor 208, and communicate optical, thermal, physical, and/or chemical data gathered about the substances to the processor 208. Light detecting devices may comprise fiber optic detectors as part of a fiber optic spectrometer system, spectrophotometers, infrared emission detectors, etc.

The processor 208 may be further adapted to calculate the pH of the substance in the compartment 201 by utilizing information gathered from the monitoring device 202. With reference to FIG. 2, the processor 208 may utilize ultraviolet absorbance (herein after spectral data) to calculate pH, based on the observation that the spectral data for a given substance is pH dependant. This technique comprises producing a mathematical model correlating the pH of a substance X to the spectral data of a substance X at one or more wavelengths, and loading the information into the processor 208. The processor 208 may then compare UV absorbance data gathered from the monitoring device and use the above referenced mathematical model to calculate the pH of the substance.

To correlate the spectral data of substance X with its pH, the pH of at least one separately prepared sample of substance X, at a known concentration, is obtained using current invasive methods (e.g., by pH probe or an indicator dye) along with its spectral data. Generally the separately prepared sample is prepared at a prior time and its pH value and spectral data stored in the processor for reference in the correlation step. Given the observation that the absorbance spectra for a given substance is pH dependent at a fixed concentration, by comparing the spectral data of substance X at an unknown pH with that of spectral data of substance X at a known pH, the pH value of the unknown sample can be determined. While it is possible to directly correlate pH with absorbance at a single wavelength, to ensure the accuracy and precision of the correlation, it may be desirable to measure the absorbance of the substance X at two or more wavelengths. Further, if the concentration of substance X is an unknown variable or if substance X is a mixture of substances, obtaining absorbance spectra over a range of wavelengths and concentrations may be desirable.

The mathematical model thus obtained, may make it possible to rapidly and accurately determine the pH of the substance in noninvasive optical pH tests of the substance, enabling the substance to be part of an entirely closed system thereby ensuring the safety and efficacy of the substance, and further ensuring zero substance loss. The substance of interest for noninvasive optical pH testing may be, but is not limited to, substances containing organic acids such as carboxylic acids and their corresponding salts. Common carboxylic acids are formic acid, acetic acid, propionic acid, butyric acid, valeric acid, caproic acid, enanthic acid, caprylic acid, pelargonic acid, capric acid, lauric acid, stearic acid, lactic acid, citric acid, adipic acid or pyruvic acid and any combination thereof.

Figure 3A:
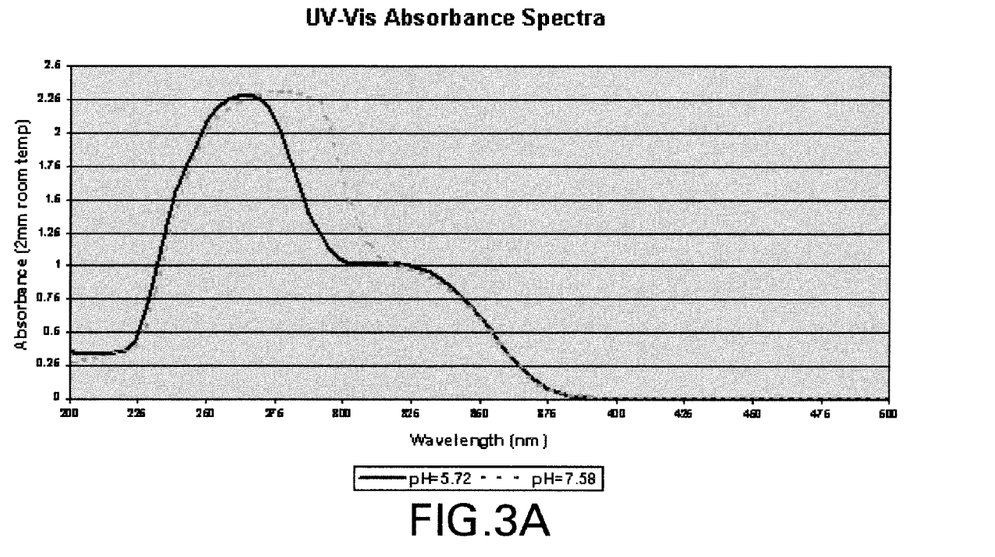
FIG. 3a is an exemplary example of a spectral curve taken from two different pyruvate solutions, which have similar concentration of pyruvic acid but different pH values.
Figure 3B:
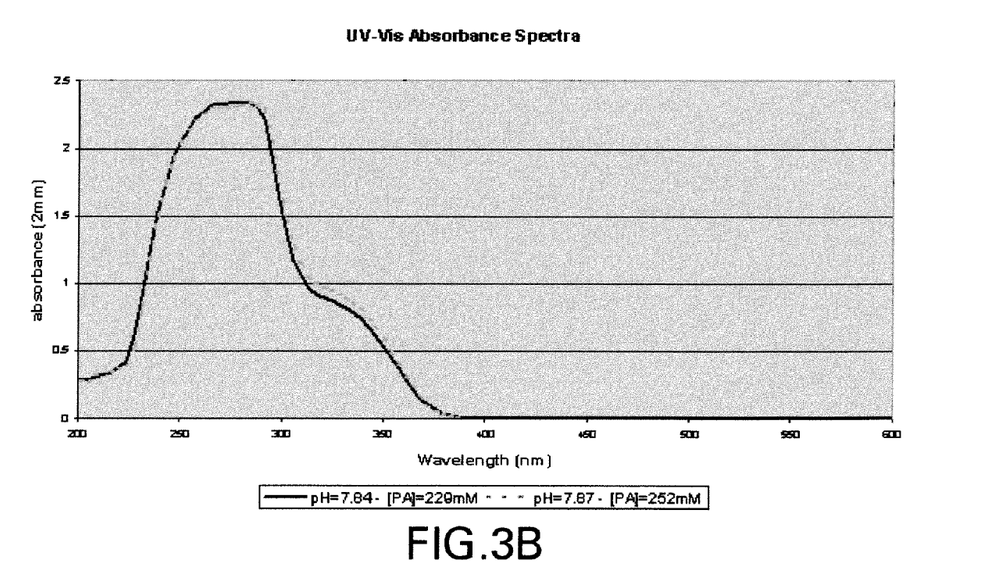
FIG. 3b is an exemplary example of a spectral curve taken from two different pyruvate solutions, which have similar pH values but different concentrations of pyruvic acid.

In an exemplary embodiment of the invention, the substances of interest are buffer solutions of pyruvic acid and/or sodium pyruvate with optical absorption data gathered using wavelengths from about 200 nm to 500 nm. In FIG. 3a, the spectral curves taken from two different pyruvate solutions are shown which have similar concentration of pyruvic acid but different pH values. The shapes of the absorption spectral curves in FIG. 3a are different, most markedly from around 250 nm to 325 nm, and correspond to a change in the spectral properties of the solution but the measurement of UV absorption intensities are relatively the same. In FIG. 3b, the absorption spectra of two pyruvate solutions having the same pH but different concentrations of pyruvic acid are shown. Here, the shapes of the spectral curves are comparable, but the relative UV absorbance intensities differ markedly from about 300 nm to 350 nm, and relate to changes in the molar absorptivity of the substances.

In some embodiments of the invention using statistical analysis tools, a mathematical model may be created correlating the intensity of UV absorption at one or more wavelengths to the pH value and concentration of the solution. Various statistical analysis tools for creating a mathematical model are available and well known in the arts such as, but not limited to, multiple linear regression analysis, modified covariance simulations, model based simulation and principal component analysis simulation. Applying the mathematical model thus created to spectral data obtained from a given pyruvate solution, it is possible to determine the pH of the given solution.

Figure 3C:
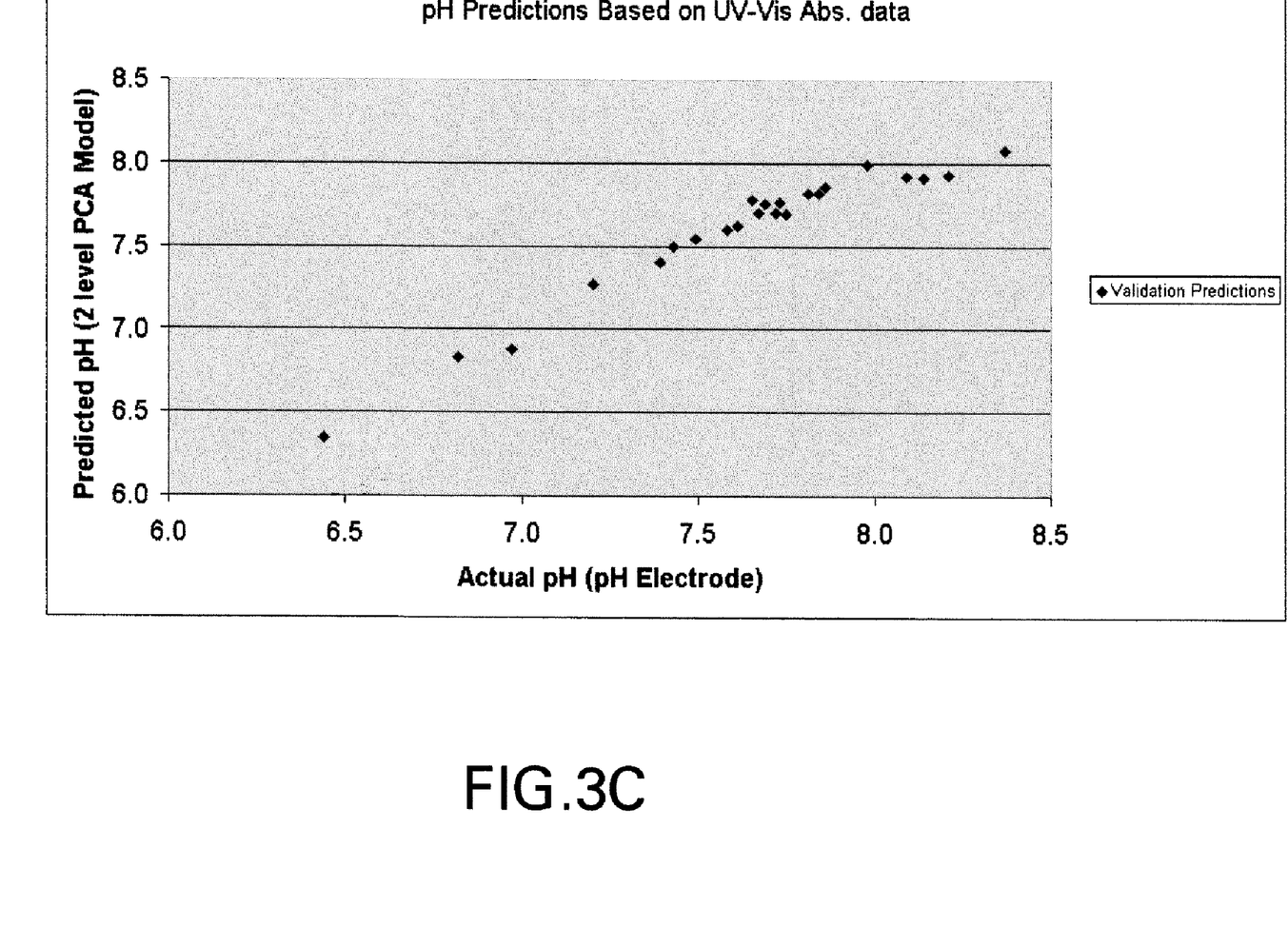
FIG. 3C is an exemplary example of predicted pH values versus actual pH values of pyruvate solutions calculated using a two level principal component analysis.

An exemplary embodiment of the invention is shown in FIG. 3c. which shows predicted pH values versus actual pH values of pyruvate solutions using a two level principal component analysis whereby the relationship between pH value and UV absorbance was simulated.

Figure 4:
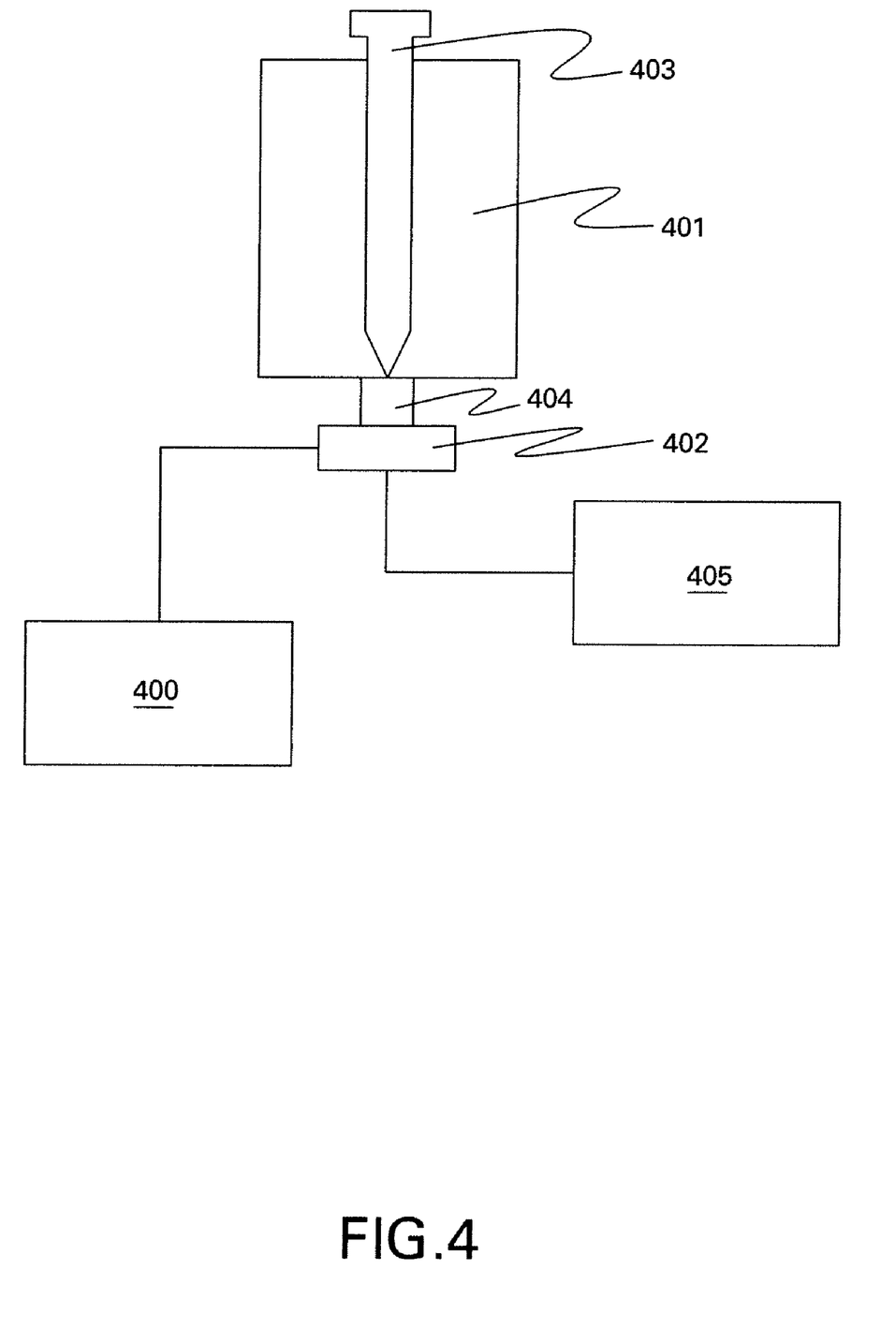
FIG. 4. depicts an exemplary embodiment of a release mechanism comprising a physical barrier and a needle and septum, wherein the physical barrier is configured to allow the needle to pierce the compartment to release the substance if appropriate QC values are obtained.

Referring to FIG. 4, an embodiment for controlling the release of a substance is shown (e.g., if the pH is appropriate). The processor 400 is coupled to release mechanism 402 which functions with the compartment 401 to release the substance to its end-use 405. The exemplary release mechanism shown in FIG. 4 comprises a needle 403 and septum 404. In this particular exemplary embodiment, the processor 400 may be configured to signal the injection of the needle 403 into the compartment 401, therein permitting the release of the substance to its end-use when one or more end-use acceptable QC values are obtained. Conversely, if the selected values for the chosen properties do not meet the chosen end-use value(s), the processor 400 will not signal the injection of the needle 403 into the compartment 401, thereby insuring that if the substance does not pass QC, it will not be released to its end-use. The operator (not shown) may have the ability to select which values, and for which properties e.g., pH, concentration, volume, etc. the processor 400 may evaluate before releasing the substance to its appropriate end-use. As used herein "operator" refers to a person, for example a clinician, who may in some embodiments of the present invention, choose QC properties and values for the QC apparatus to test. In other embodiments, the clinician merely initiates the process, and has no interactive control over the QC apparatus post-initiation. In this particular embodiment, the QC properties and values may be pre-set, for example by a regulatory committee, because it may be preferable for QC properties and values to be inaccessible to the operator thereby lessening the probability of operator error.

Generally, either the substance passes all of the appropriate QC tests and is released from the compartment 401, or it fails one or more tests and is not released. It is to be appreciated that the release mechanism 402 may also comprise a valve, a hatch, a tap, a spigot, mechanical needles or levers, restraining arms or bars, etc. Naturally, an operator may be used to initiate the process in any embodiment, e.g., by pressing a button or issuing a start command to the QC apparatus.

Figure 5:
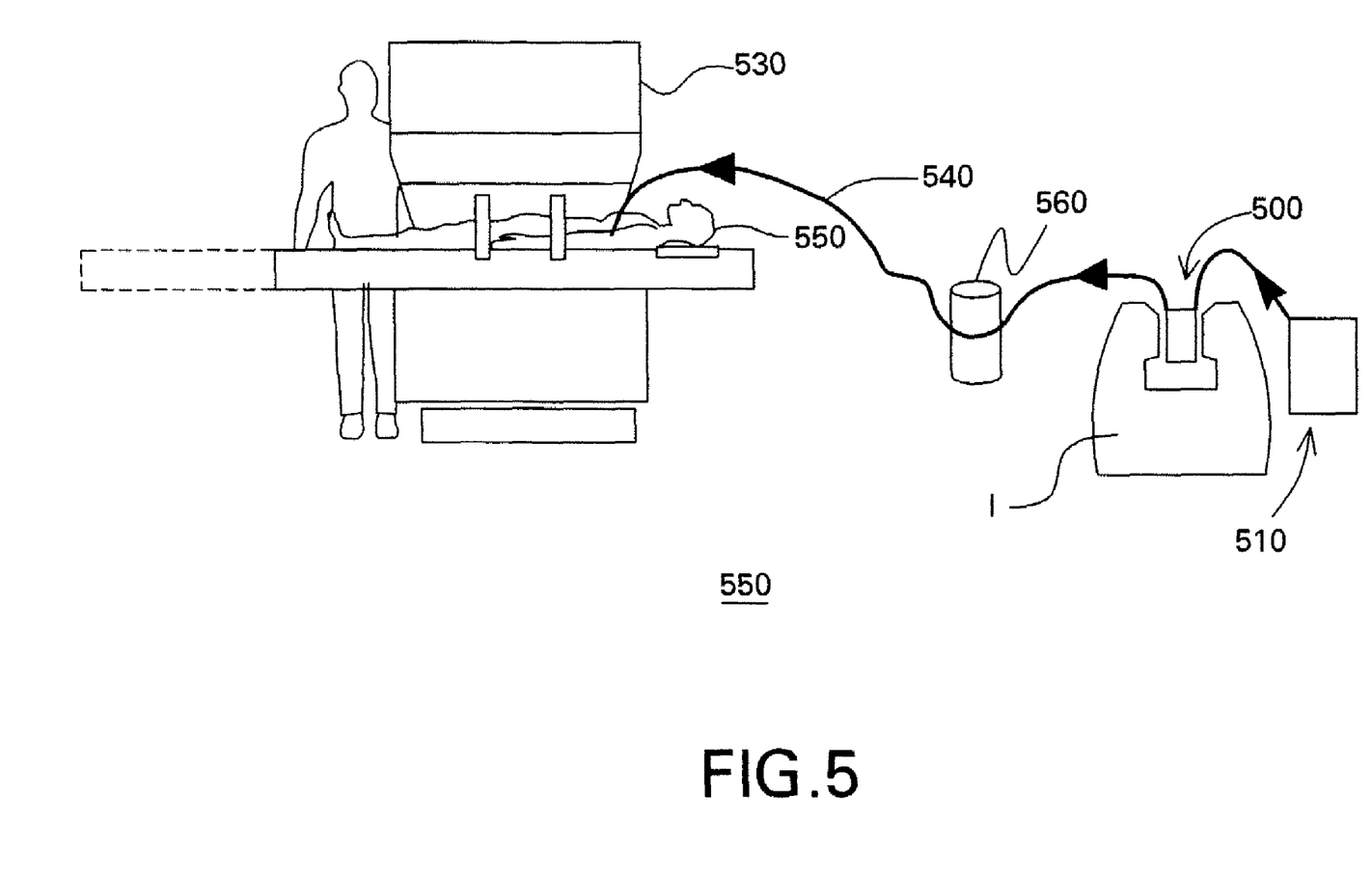
FIG. 5 is an illustration of an exemplary MRI system and polarizing subsystem for which embodiments of the present invention are applicable.

FIG. 5 is an illustration of an exemplary MRI system and polarizing subsystem for which embodiments of the present invention may also be applicable.

Referring to FIG. 5, a exemplary system 550 is shown for producing hyperpolarized samples for use in a MRI device and includes a cryostat 1 and polarizing subsystem 500 for processing material from container 510 and resulting in the hyperpolarized material. A material delivery line 540 is used to deliver the hyperpolarized material to subject 550 within MRI scanner 530. In the embodiment shown in FIG. 5, the hyperpolarized samples are used in an in vivo imaging application, where the hyperpolarized samples must undergo automated QC analysis to ensure that proper efficacy and safety standards are met before the product is released for patient delivery through line 540

Referring further to FIG. 5, container 510 contains a solid sample of the sample to be polarized can be polarized while still in the solid phase by any appropriate known method, e.g. brute force polarization, dynamic nuclear polarization or the spin refrigerator method, while being maintained at a low temperature (e.g. under 100 K) in a strong magnetic field (e.g. 1-45 T). After the solid sample has been polarized, it is melted with a minimum loss of polarization. In the following the expression "melting means" will be considered to mean the following: a device capable of providing sufficient energy to the solid polarized sample to melt it or otherwise bring the polarized sample into solution for introduction into the subject being imaged. As used herein, the term "solid" refers to solid materials; semi-solid materials or any combination thereof provided the material requires some transformation to attain a liquid state suitable for introduction into a subject being imaged.

When the polarized material is in its liquid state, held in polarized sub-system 500, embodiments of the present invention are applicable. In this exemplary embodiment, $^{13}$C pyruvate in polarized form is the substance to be used during in vivo imaging, and is therefore also the substance subject to QC analysis, which may take place in receiving compartment 560 of the polarized subsystem. One particular aspect of QC analysis is accurately determining the pH of the pyruvate solution using the method and system of the present invention.

Although the preceding example is a medicinal use the invention is not limited to medicinal uses. There are also industrial uses, such as assembly lines and food processing, pharmacological uses, any instance where material loss is an issue, etc.

While only certain features of the invention have been illustrated and described herein, many modifications and changes will occur to those skilled in the art. It is, therefore, to be understood that the appended claims are intended to cover all such modifications and changes as fall within the true spirit of the invention.

We claim:

1. A noninvasive optical method for determining pH of a solution of a substance in a compartment within a closed system comprising:
   obtaining spectral data for the solution of a substance in a compartment for at least one wavelength;
   correlating the spectral data obtained from the compartment solution and spectral data for a separately prepared solution with a known pH value corresponding to the at least one wavelength;
   predicting the pH of the compartment solution; and
   controlling the release of the solution of a substance from the compartment to its end-use based on the predicted pH.

2. The method of claim 1, wherein the obtaining the spectral data step comprises directing light through a solution of a substance to measure the light absorbance of the solution at one or more wavelengths.

3. The method of claim 1, wherein the correlating step is determined by a mathematical model comprising determining a statistical relationship between the spectral data of a solution of a substance and its pH value.

4. The method of claim 1, wherein the solution of the substance comprises an organic acid, its corresponding salt and any combination thereof.

5. The method of claim 4 wherein the organic acid is a carboxylic acid selected from pyruvic acid, formic acid, acetic acid, propionic acid, butyric acid, valeric acid, caproic acid, enanthic acid, caprylic acid, pelargonic acid, capric acid, lauric acid, stearic acid, lactic acid, citric acid, adipic acid and any combination thereof.

6. The method of claim 5 wherein the organic acid or its corresponding salt is pyruvic acid, sodium pyruvate and any combination thereof.

7. The method of claim 6, wherein the solution of the substance further comprises sodium hydroxide, ethylenediaminetetraacetic acid disodium salt and tris(hydroxymethyl) aminomethane in water.

8. The method of claim 1, wherein the at least one wavelength is in the range from about 200 nm to about 500 nm.

9. The method of claim 1 wherein the at least one wavelength is in the range from about 250 nm to about 400 nm.

10. The method of claim 1 wherein the at least one wavelength is in the range from about 280 nm to about 320 nm.

11. The method of claim 1, wherein the method is functionally adapted for integration into a sterile substance path, wherein the method operates to determine pH of a substance and further ensure the sterility of a substance in the sterile substance path.

12. The method of claim 11, wherein the determination of pH further comprises an initiation step preformed by an operator and wherein subsequent steps are fully automated.

13. A system for determining pH of a solution of a substance comprising:
   a compartment capable of holding a solution of a substance and which is permeable to at least one wavelength of light;
   a light source and light detecting device configured to obtain spectral data for the solution of the substance at one or more wavelengths;
   a processor adapted to determine the pH value of the solution of the substance by correlating the spectral data obtained with separately obtained spectral data at the same one or more wavelengths for at least one solution of the substance at a known pH value; and a release mechanism to release the substance to its end-use.

14. The system of claim 13 wherein the light detecting device measures light absorbance of the solution of a substance at one or more wavelengths.

15. The system of claim 13, wherein the processor is further adapted to employ a mathematical model wherein the model comprises determining a statistical relationship between a substance's spectral data and pH wherein the statistical relationship facilitates pH determination during noninvasive optical pH testing of a solution of the substance.

16. The system of claim 13, wherein the at least one substance comprises an organic acid, its corresponding salt, and any combination thereof.

17. The system of claim 16 wherein the organic acid is a carboxylic acid selected from pyruvic acid, formic acid, acetic acid, propionic acid, butyric acid, valeric acid, caproic acid, enanthic acid, caprylic acid, pelargonic Acid, capric acid, lauric acid, stearic acid, lactic acid, citric acid, adipic acid and any combination thereof.

18. The system of claim 17 wherein the organic acid or its salt is pyruvic acid, sodium pyruvate and any combination thereof.

19. The system of claim 18, wherein the solution of the substance further comprises sodium hydroxide, ethylenediaminetetraacetic acid disodium salt and tris(hydroxymethyl) aminomethane in water.

20. The system of claim 13, wherein the at least one or more wavelengths is in the range from about 200 nm to about 500 nm.

21. The system of claim 13, wherein the at one or more wavelengths is in the range from about 250 nm to about 400 nm.

22. The system of claim 13, wherein the at one or more wavelengths is in the range of from about 280 nm to about 320 nm.

23. The system of claim 13, wherein the system is functionally adapted for integration into a sterile substance path, wherein the system operates to determine pH and further to ensure sterility of a substance in the sterile substance path.

24. The system of claim 13, wherein the processor further functions to allow an initiation step preformed by an operator and wherein subsequent steps are fully automated.

25. The system of claim 13, wherein the release mechanism operates to release the fluid from the compartment to its end use if the pH is within a predetermined range.

* * * * *